United States Patent [19]

Prosperi et al.

[11] 4,100,029

[45] Jul. 11, 1978

[54] METHOD FOR IMPROVING THE ACTIVITY OF OXIREDUCTASE ENZYMES EMBEDDED IN FILAMENTARY STRUCTURES

[75] Inventors: Giulio Prosperi, Rome; Walter Marconi, San Donato Milanese (Milan); Silvia Giovenco, Rome; Franco Morisi, San Giovanni in Persiceto (Bologna), all of Italy

[73] Assignee: Snam Progetti S.p.A., San Donato Milanese, Italy

[21] Appl. No.: 703,968

[22] Filed: Jul. 9, 1976

[30] Foreign Application Priority Data

Jul. 10, 1975 [IT] Italy ............................... 25251 A/75

[51] Int. Cl.$^2$ ................................................. C07G 7/02
[52] U.S. Cl. ............................... 195/68; 195/DIG. 11; 195/63
[58] Field of Search ................... 195/68, 63, DIG. 11

[56] References Cited

U.S. PATENT DOCUMENTS

| 3,715,277 | 2/1973 | Dinelli et al. | 195/63 |
| 3,947,325 | 3/1976 | Dinelli et al. | 195/68 |
| 3,957,748 | 5/1976 | Weetall | 195/63 X |
| 4,004,980 | 1/1977 | Emery et al. | 195/68 |

*Primary Examiner*—Lionel M. Shapiro
*Attorney, Agent, or Firm*—Morgan, Finnegan, Pine, Foley & Lee

[57] ABSTRACT

A method is disclosed for improving the activity of oxireductase enzymes, the improvement consisting in that an enzyme and a previously functionalized coenzyme are embedded in a filamentary structure, the coenzyme having previously been attached to a water-soluble, high-molecular-weight polymer.

6 Claims, No Drawings

METHOD FOR IMPROVING THE ACTIVITY OF OXIREDUCTASE ENZYMES EMBEDDED IN FILAMENTARY STRUCTURES

This invention relates to a method for improving the activity of oxidoreductase enzymes embedded in filamentary structures by a simultaneous occlusion of both enzyme and coenzyme.

It is known that enzymes can be immobilized with a number of procedures on water-insoluble supports and can then be used as heterogeneous catalysts which can easily be separated from the reaction mixture and can thus be reused.

In the case of enzymes, or enzymic complexes which require a coenzyme of the $NAD^+$ type, it was required that said coenzyme was added to the reaction mixture. As a matter of fact, on account of the low molecular weight of the coenzyme, it is difficult to immobilize it together with the enzyme on the same support so as to render the continuous addition of same coenzyme to the reaction mixture unnecessary.

In addition, covalent bonding on the coenzyme to the support itself to which the enzyme is attached is unadvisable due to steric hindrances which prevent or drastically limit the interactions between the enzyme and the coenzyme, said interactions being required for activity.

Inasmuch as such coenzymes are comparatively expensive, the fact of being compelled to add them continuously to a reaction mixture, was a drastic limit to the use of oxidoreductase systems in fiber form.

It is likewise known that $NAD^+$ can be functionalized in the 6-amino purinic group and the functionalized $NAD^+$ can be attached to water-soluble, high-molecular-weight polymers, according to methods which have been disclosed in the U.S. Pat. No. 4,008,363 and application Ser. No. 586,354 in the name of the same assignee hereof.

The present applicants have now found that such polymers which have a coenzymic activity can be occluded in water-insoluble polymeric matrices, more particularly filamentary structure, together with an enzyme.

The simultaneous occlusion of enzymes and coenzymes involves a stabilization of the oxidoreductase, which, when no coenzyme is present, undergo equilibria of associations and dissociations of the sub-units, the result being an activity loss.

The practice of this invention permits to prepare a polyenzymic biological reagent in which the polymeric derivative of $NAD^+$ is continuously cycled from the oxidized form to the reduced form, at the expenses of two oxidoreductases. The $NAD^+$ derivative can be cycled not only by the enzymic way, using two oxidoreductases, but also by the combined chemical and enzymic way, by utilizing an oxidoreductase and a chemical compound. The recycle system is selected consistently with the product which one desires to obtain.

The way in which enzyme and coenzyme can be occluded is that described in U.S. Pat. No. 3,715,227 of the same assignee hereof and reference is invited thereto for any further technical details. The structure comprises a fibrous or filamentous structural base of artificial or synthetic polymeric material and the required enzymes or enzymatic preparation therein englobed and subdivided and partially enclosed in small alveoli or separated cavities.

The applications of macromolecular coenzymes which can be embedded together with enzymes in polymeric matrices make up a wide variety. In the preparative chemistry syntheses of steroids or transformations of steroidal nuclei in preselected positions; in addition, stereospecific syntheses can be carried out, of amino acids starting from hydroxyacids or ketoacids. In the analytical field, it is possible to occlude enzyme-coenzyme systems in which the ultimate reaction of oxidation of the reduced coenzyme, or of reduction of the oxidized coenzyme, is carried out by a chemical substance the absorption spectrum of which is a function of the reduced, or oxidized, state in which it lies. The color of such a substance can easily be measured and correlated to the quantity of the substance sought for.

The ensuing examples are intended better to illustrate the invention, without, however, limiting it.

EXAMPLE 1

For the occlusion, there is available an enzyme solution in buffer and glycerol (75:25) of polyethyleneimine-$NAD^+$ (PEI-$NAD^+$), Lacticdehydrogenase (LDH) (from rabbit, Boehringer, Mannheim, GmbH) and alanine-dehydrogenase (Ala DH) (from *B. subtilis*, Boehringer, Mannheim, GmbH), with the following specifications:

PEI-$NAD^+$ 37.5 milligrams/ml (= 0.63 micromols $NAD^+$ per ml)

LDH 17.5 mgm/ml (70 I.U., $NAD^+$ as the substrate)

Ala DH 3.75 mgm/ml 10 grams of cellulose triacetate (Fluka AG., Buchs) are dissolved, with stirring in a reactor, in 133 grams of methylene chloride. 20 grams of the enzyme solution are added to the polymer solution and the emulsification of the two phases is encouraged by a vigorous stirring at 0° C (zero centrigrade) during 30 minutes.

The emulsion is poured in a small melting pot kept at 0° C and spun under nitrogen pressure.

The filament is coagulated in toluene at 0° C and collected on a bobbin frame.

Air-drying is carried out to remove the organic solvents. 2 grams of the thusly obtained fiber, which correspond to about 1 gram of dry polymer, are washed with a pH 8.0 bicarbonate buffer to remove the enzymes and PEI-$NAD^+$ which have been adsorbed on the surface, and then the fiber is placed in 10 mls of an aqueous solution having the following composition:

Ammonium L-lactate at 3% (weight to volume) at a pH 7.4.

Stirring at room temperature (22° C approx.) is carried out. After 10 hours, by means of an aminoacid autoanalyzer, the quantity of as formed L-alanine is measured, which amounts to 0.163 grams (96% of theory).

Once the mixture has been discharged, the same fiber is contacted with a fresh solution of ammonium lactate for a fresh reaction cycle. After a 7-day run, the percentage of L-alanine is 94%, at 10 hours and after 30 days, still at 10 hours, it is 90%. L-alanine is separated by precipitation with ethanol at a pH of 6.2. $[\alpha]_D^{25} = +14.6°(c = 2.0; 5N\ HCl)$.

EXAMPLE 2

A fiber is prepared as in Example 1 by using instead of PEI-$NAD^+$, the Formyl-PEI-$NAD^+$.

2 grams of the thus obtained fiber, corresponding, roughly, to 1 gram of dry polymer, are washed with a 0.05 M, pH 8.0 phosphate buffer and placed in 10 mls of an aqueous solution having the following composition: 0.05M, pH 8 phosphate buffer which contains 5% (weight to volume) ammonium DL-lactate. After 10 hours the formed alanine is 98% of theory. The same fiber is placed again in 10 milliliters of the solution and the solution is changed every eleventh hour. After 30 days of continuous operations the percentage of alanine as formed at 10 hours is 95%.

EXAMPLE 3

A fiber is prepared as in Examples 1 and 2 by using Polylysine-NAD$^+$. By operating in the same manner as in Examples 1 and 2, at 10 hours the 92% of the theory of alanine is obtained. After 30 days of use of the same fiber, an 87% conversion is obtained.

EXAMPLE 4

There is available, for the occlusion, a solution of buffer-glycerol (75/25) which contains:
Polyethyleneimine-NAD$^+$:25.5 mgm/ml (3.78 micromols NAD$^+$/ml). 3 alpha, 20 beta-hydroxysteroid dehydrogenase (from *Streptomyces hydrogenans*, Boehringer, Mannheim, GmbH): 12.5 mgm/ml (225 units/ml; 25° C; cortisone as the substrate). Alcohol dehydrogenase (ADH) (from horse's liver, Boehringer, Mannheim, GmbH): 30 mgm/ml (81 units/ml; 25° C; ethanol as the substrate). Aldehyde dehydrogenase (from yeast, Sigma, St. Louis): 30 mgm/ml (90 units/ml; 25° C; acetaldehyde as the substrate).

A fiber is prepared as in Example 1.

2 grams of fiber, corresponding to about 1 gram of dry polymer are stirred at 25° C with 10 mls of solution in triethanolamine hydrochloride buffer (0.1 M, pH 7.3) which contains: KCl (0.3 M), 5mM beta-mercaptoethanol, 1% ethanol, so as to remove the substances which have been adsorbed at the surface to have a stabilizing medium for the activity which has been embedded.

On completion of the washing, due to the action of the alcohol dehydrogenase and aldehyde dehydrogenase, the PEI-NAD$^+$ is converted into its reduced form.

The washing liquor is removed by filtration and there are added 10 mls of the same buffer solution which contain 28 mg of cortisone (Δ 4-pregnene-17 alpha, 21-diol-3,11,20-trione).

The solution is kept stirred at 25° C during 1 hour, whereafter the mixture is discharged. The solution is extracted thrice with 2 mls of chloroform each time. The organic extract is concentrated in a vacuo to a volume of 1 ml. By gaschromatographic analysis the quantity of the product (Δ 4-pregnene-17 alpha, 20 beta, 21-triol-3,11-dione) and the cortisone are determined. A conversion of 95% has been calculated.

The same fiber sample has been used for twenty cycles of conversion of cortisone, with a negligible activity drop.

EXAMPLE 5

There is, available for the occlusion, a solution in buffer and glycerol (75:25) which contains:
Polyethyleneimine-NAD$^+$:25.5 mgm/ml (3.78 micromol NAD$^+$/ml) beta-hydroxysteroid dehydrogenase (from "*Pseudomonas testosteroni*", grade II, Sigma, St. Louis) : 40 mgm/ml. diaphorase (from pig's heart, grade II, Boehringer, Mannheim, GmbH) : 19.4 mgm/ml of the commercial product (containing 6.45 mgm/ml of enzymic protein).

A fiber such as in Example 1 is prepared.

2 grams of fiber, corresponding to 1 gram of dry polymer are washed with a triethanolamine hydrochloride buffer, 0.067 M, pH = 7.6, to remove the substances which had been adsorbed on the surface and placed in 10 mls of an aqueous solution containing: triethanolamine hydrochloride buffer, 0.067 M, pH = 7.6, 288 micrograms of testosterone (17 beta-hydroxy-Δ4-androstene-3-one), 2.9 mgm of 2,6-dichloro phenolindophenol. The solution is stirred at 25° C and oxygen is bubbled to oxidize the reduced dyestuff again. After 4 hours the mixture is extracted three times with 3 mls of ethyl acetate each time. The organic extract is dehydrated with anhydrous sodium sulphate, filtered and evaporated to dryness. The solid residue is dissolved in 0.5 ml of methanol. The quantity of the product (Δ4-androstene-3,17-dione) which has been formed, is 90% of the starting testosterone.

EXAMPLE 6

The same fiber as in Example 5 has been used. One gram of fiber, corresponding to 0.5 gram of dry polymer has been washed with triethanolamine hydrochloride buffer 0.06 M, pH = 7.6 to remove the substances which had been adsorbed on the surface.

Five solutions have been prepared, which contained triethanolamine hydrochloride buffer 0.06 M, pH = 7.6, 2,6-dichlorophenolindophenol, 80 micromols, and testosterone (17 beta-hydroxy-Δ4-androstene-3-one:10 micromols, 20 micromols, 30 micromols, 40 micromols and 50 micromols.

The gram of the washed fiber has been placed, each time, in 5 mls of each solution and the mixtures have been stirred at 25° C measuring the absorbance at 600 mm. A calibrating straight line has been drawn with the differences of optical density and the concentrations of testosterone. The same fiber has repeatedly been used for metering the testosterone in the solution which contained it in a concentration of 30 micromols. During 100 readouts no deviations have been detected from the value of the calibration line.

What we claim is:

1. A method for improving the activity of oxidoreductase enzymes that are formed into a filamentary structure which comprises a fibrous or filamentous structural base of a water-insoluble artifical synthetic polymeric material and an enzyme or enzymes therein englobed and subdivided and partially enclosed in separated alveoli, said method comprising the steps of forming solutions of a structural base of a water-insoluble artifical synthetic polymeric material an oxidoreductase enzyme and a coenzyme of nicotinamide-adenine-dinucleotide and a water soluble, high molecular weight polymer, forming an emulsion of said solutions and thereafter spinning said emulsion into said filamentary structure.

2. The method of claim 1 wherein the filamentary structure is derived from a fibrous structural base which comprises cellulose triacetate and polyethyleneimine-nicotinamide-adenine-dinucleotide and the enzymes are lacticdehydrogenase and alanine-dehydrogenase.

3. The method of claim 1 wherein the filamentary structure is derived from a fibrous structural base which comprises cellulose triacetate, formylpolyethyleneimine-nicotinamide-adenine-dinucleotide and the enzymes are lacticdehydrogenase and alanine-dehydrogenase.

4. The method of claim 1 wherein the filamentary structure is derived from a fibrous structural base which comprises cellulose triacetate, polylysine-nicotinamide-adenine-dinucleotide and the enzymes are lacticdehydrogenase and alanine-dehydrogenase.

5. The method of claim 1 wherein the filamentary structure is derived from a fibrous structural base which comprises cellulose triacetate polyethyleneimine-nicotinamide-adenine-dinucleotide, beta-hydroxysteroid dehydrogenase, alcohol dehydrogenase and aldehyde dehydrogenase.

6. The method of claim 1 wherein the filamentary structure is derived from a fibrous structural base which comprises cellulose triacetate, polyethyleneimine-nicotinamide-adenine-dinucleotide, beta-hydroxysteroid dehydrogenase and diaphorase.

* * * * *